US009498177B2

(12) United States Patent
Bruder et al.

(10) Patent No.: US 9,498,177 B2
(45) Date of Patent: Nov. 22, 2016

(54) CONTRAST-DEPENDENT REGULARIZATION STRENGTH IN THE ITERATIVE RECONSTRUCTION OF CT IMAGES

(75) Inventors: Herbert Bruder, Höchstadt (DE); Thomas Flohr, Uehlfeld (DE); Rainer Raupach, Heroldsbach (DE); Martin Sedlmair, Forchheim (DE); Heinrich Wallschlager, Erlangen (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 1189 days.

(21) Appl. No.: 12/729,272

(22) Filed: Mar. 23, 2010

(65) Prior Publication Data

US 2010/0246917 A1 Sep. 30, 2010

(30) Foreign Application Priority Data

Mar. 25, 2009 (DE) ........................ 10 2009 014 723

(51) Int. Cl.

| | |
|---|---|
| ***G06K 9/00*** | (2006.01) |
| ***A61B 6/00*** | (2006.01) |
| ***A61B 6/03*** | (2006.01) |
| ***G06T 11/00*** | (2006.01) |

(52) U.S. Cl.

CPC ............... *A61B 6/481* (2013.01); *A61B 6/032* (2013.01); *A61B 6/4014* (2013.01); *A61B 6/4441* (2013.01); *A61B 6/482* (2013.01); *A61B 6/504* (2013.01); *G06T 11/006* (2013.01); *A61B 6/503* (2013.01); *A61B 6/507* (2013.01); *A61B 6/541* (2013.01); *G06T 2211/424* (2013.01)

(58) Field of Classification Search

CPC ............................... G06T 5/002; G06T 5/007

See application file for complete search history.

(56) References Cited

U.S. PATENT DOCUMENTS

| | | | | |
|---|---|---|---|---|
| 6,697,534 | B1 * | 2/2004 | Tan et al. | 382/261 |
| 7,386,088 | B2 * | 6/2008 | Deman et al. | 378/4 |
| 2003/0053669 | A1 * | 3/2003 | Suri et al. | 382/130 |

(Continued)

FOREIGN PATENT DOCUMENTS

| | | |
|---|---|---|
| DE | 102007007803 A1 | 8/2008 |
| DE | 102008053108 A1 | 12/2009 |

OTHER PUBLICATIONS

Combining Analytical and Iterative Reconstruction in Helical Cone-Beam CT Johan Sunnegardh; Others; 2007; SE.

Fast Implemetations of Algebraic Methods for Three-Dimensional Reconstruction from Cone-Beam Data Klaus Muller . . . IEEE Transactions on Medical Imaging, vol. 18; Others; 1999.

(Continued)

*Primary Examiner* — Robert Sorey
*Assistant Examiner* — Kristine Rapillo
(74) *Attorney, Agent, or Firm* — Harness, Dickey & Pierce, P.L.C.

(57) ABSTRACT

A method is disclosed for reconstructing image data of an examination object from measured data, the measured data being captured during a rotating movement of a radiation source of a computed tomography system around the examination object. In at least one embodiment, different iteration images of the examination object are determined successively from the measured data by way of an iterative algorithm, wherein with the iterative algorithm the current iteration image at any one time is high-pass-filtered and weighted as a function of contrast using a variable which contains contrast information relating to the current iteration image at that time.

18 Claims, 3 Drawing Sheets

(56) References Cited

U.S. PATENT DOCUMENTS

| | | | | |
|---|---|---|---|---|
| 2003/0097057 | A1* | 5/2003 | Oshio et al. | 600/410 |
| 2006/0109949 | A1* | 5/2006 | Tkaczyk et al. | 378/4 |
| 2007/0110290 | A1* | 5/2007 | Chang et al. | 382/128 |
| 2008/0212741 | A1 | 9/2008 | Haras | |
| 2008/0273656 | A1* | 11/2008 | Ziegler et al. | 378/19 |
| 2009/0324044 | A1 | 12/2009 | Grasruck et al. | |

OTHER PUBLICATIONS

An Improved Algorithm for Reprojecting Rays Through Pixel Images Peter M Joseph IEEE Transactions on medical imaging; Others; 1982.

Nonlinear Regularization of Iterative Weighted Filtered Backprojection for Helical Cone-Beam CT IEEE Nuclear Science Symposium Conference Record NSS '08, 2008, pp. 5090-5095 ISSN 1082-3654 Sunnegardh, J., Grasruck, M.; Magazine; 2008.

* cited by examiner

C1
C4
C2
C3
C5
C6
C9
C11
C12
C8
P
AS
24
Prg1-Prgn
C10
P
f
C23
C21
C22

C1
C2
C7
C6
C9
C8
C11
C3
C12
AS
P
Prg1-Prgn
C10
P
f
C23
C21
C22
24

CONTRAST-DEPENDENT REGULARIZATION STRENGTH IN THE ITERATIVE RECONSTRUCTION OF CT IMAGES

PRIORITY STATEMENT

The present application hereby claims priority under 35 U.S.C. §119 on German patent application number DE 10 2009 014 723.3 filed Mar. 25, 2009, the entire contents of which are hereby incorporated herein by reference.

FIELD

At least one embodiment of the invention generally relates to a method for reconstructing image data of an examination object from measured data captured by a computed tomography system.

BACKGROUND

Methods for scanning an examination object by way of a CT system are generally known. In such cases use is made of, for example, circular scans, sequential circular scans with feeding movement, or spiral scans. In these scanning operations absorption data of the examination object are recorded from different recording angles with the aid of at least one X-ray source and at least one oppositely disposed detector and said thus collected absorption data or projections are computed by means of appropriate reconstruction methods into sectional images (slices) through the examination object.

A method referred to as filtered back projection (FBP) is used at the present time as the standard method for reconstructing computed tomography images from X-ray CT datasets of a computed tomography device (CT device), i.e. from the captured projections. With said method the data are first preprocessed in order to remove as much noise from them as possible. Next a so-called "rebinning" step is performed in which the data generated by means of the beam propagating itself from the source in a fan shape is re-formed in such a way that they are present in a form as though the detector were struck by an X-ray wave front converging in parallel onto the detector.

The data are then transformed into the frequency domain. Filtering takes place in the frequency domain and then the filtered data are back-transformed. With the aid of the data re-sorted and filtered in this way a back-projection onto the individual voxels within the volume of interest is performed. The traditional FBP methods are, however, subject to problems with (low-frequency) cone beam artifacts and spiral artifacts due to their approximative principle of operation. Furthermore, with traditional FBP methods the image sharpness is linked to the image noise. The higher the image sharpness achieved, the higher also is the image noise and vice versa.

In more recent times, therefore, iterative reconstruction methods have been developed by which at least some of these limitations can be removed. With an iterative reconstruction method of said kind a reconstruction of initial image data from the projection measured data is performed first. Toward that end a convolution back-projection method can be used, for example. Synthetic projection data are then generated from said initial image data by means of a "projector", i.e. a projection operator which should simulate the measurement system mathematically as closely as possible. The difference from the measured signals is then back-projected by means of the operator adjoint to the projector and in this way a residue image is reconstructed on the basis of which the initial image is updated. The updated image data can in turn be used in order to generate new synthetic projection data with the aid of the projection operator in a next iteration step, to form the difference from the measured signals once again from said data and to calculate a new residue image by which the image data of the current iteration step are improved, etc. With a method such as this it is possible to reconstruct image data providing high image definition while having a reduced number of artifacts.

SUMMARY

In at least one embodiment of the present invention, an improved reconstruction method is disclosed, as well as a corresponding CT system, computer program and computer program product.

With the method according to at least one embodiment of the invention image data of an examination object are reconstructed from measured data. The measured data were captured previously during a rotating movement of a radiation source of a computed tomography system around the examination object. Different iteration images of the examination object are determined successively from the measured data by way of an iterative algorithm. With this iterative algorithm the current iteration image at a given time is high-pass filtered and weighted as a function of contrast using a variable which contains contrast information relating to the current iteration image at that time.

The images that are to be acquired from the examination object can be slices through the examination object. Furthermore it is possible to determine three-dimensional images of the examination object by way of the method according to at least one embodiment of the invention.

An iterative algorithm is used for reconstructing images. Within the scope of the algorithm a first iteration image is calculated first, a second iteration image in the next iteration cycle, a third iteration image in the next iteration cycle, etc. The iteration images are calculated by applying a specific computing rule to the preceding iteration image in each case. The last of the iteration images corresponds to the reconstructed image which can be output as the result.

Within the iterative algorithm the current iteration image at a given time in each iteration cycle is subjected to high-pass filtering. The current iteration image at a given time is the image being processed in the current iteration cycle, i.e. that to which a computing rule is applied in order to obtain the next iteration image. High-pass filtering produces an edge-strengthening effect.

A specific variable is also used within the iterative algorithm. Contrast information of the current iteration image at any one time is incorporated into the variable. The variable can be used in particular in such a way that a regularization using the variable is performed for each iteration. The regularization entails a filtering of the iteration image in order to stabilize the solution. By this, grayscale values in neighborhoods of the image can be subjected to constraints.

The contrast information can be embodied in different ways. In this context the contrast is a measure for differences between values, in particular grayscale values, of images. For example, the contrast information can indicate differences between directly adjacent pixels or between pixels in a specific neighborhood. In the case of a three-dimensional image the contrast information can also indicate differences between pixels of one layer image and pixels of adjacent layer images. Suitable edge detectors can be applied to the particular image for the purpose of determining contrast information.

In a development of at least one embodiment of the invention the iterative algorithm effects a contrast-dependent noise reduction of an iteration image based on the variable. This means that a smoothing or noise reduction takes place from iteration image to iteration image, this process being initiated or influenced by the variable. The effect of the variable is such that the noise is reduced as a function of the contrast information.

It is advantageous if the variable contains location-dependent contrast information. The location dependence corresponds to a dependence on the position within an image. Since the image maps the examination object, this also corresponds to a dependence on a position within the examination object. In particular it is possible for the variable to contain contrast information for each pixel of the current iteration image at any one time. Alternatively hereto it is also possible for the variable to contain contrast information for only some pixels of the current iteration image at any one time, or for groups of such pixels.

In an embodiment of the invention the iterative algorithm effects a location-dependent noise reduction of an iteration image based on the variable, wherein the location dependence of the noise reduction is correlated with the location dependence of the contrast information. In this case the noise reduction is not uniform over the entire image, but is dependent on the contrast information which is assigned to specific positions within the image.

In a development of at least one embodiment of the invention the iterative algorithm effects a noise reduction based on the variable preferably at low-contrast locations of an iteration image. Reducing the noise at low-contrast locations means performing a smoothing in homogeneous image areas. A corollary of the fact that the noise reduction is preferably performed at low-contrast locations is that smoothing is ideally not performed or performed only to a lesser extent at high-contrast locations. By this, a contrast-rich image with little noise can be obtained as the reconstruction result.

It is advantageous if the contrast information includes a contrast-to-noise ratio. This can be embodied for example as follows: The variable is called β by way of example and is yielded as the result of $$\beta = \beta^0 e^{-\left(\frac{df}{\sigma}\right)^2}.$$

In this case $\beta^0$ is a parameter, in particular a scalar in the interval [0 1]. Furthermore $\beta^0$ can be changed from iteration cycle to iteration cycle. The variable df is a contrast value, and σ a noise value. Both variables df and σ are produced from the current iteration image at any one time.

In a development of at least one embodiment of the invention the iterative algorithm is based on an iteration equation in which the current high-pass-filtered iteration image weighted as a function of contrast is applied to the current iteration image. This means that in order to calculate the next iteration image the current iteration image and the current iteration image which has been high-pass-filtered and weighted as a function of contrast are calculated together. This calculation can be performed e.g. by means of an addition or a subtraction. In this case the variable can control in particular the degree to which the high-pass-filtered current iteration image is admixed with the current iteration image.

The CT system according to at least one embodiment of the invention comprises a control and computing unit for controlling the CT system, the detector data capture and the reconstruction of tomographic slices. It includes a program memory for storing program code, wherein there is resident herein—possibly inter alia—program code which is suitable for performing a method of the above-described type during the operation of the CT system.

The computer program according to at least one embodiment of the invention has program code segments which are suitable for performing the method of the above-described type when the computer program is executed on a computer.

The computer program product according to at least one embodiment of the invention comprises program code segment stored on a computer-readable data medium which are suitable for performing the method of the above-described type when the computer program is executed on a computer.

BRIEF DESCRIPTION OF THE DRAWINGS

The invention is explained in more detail below with reference to an example embodiment and the attached drawings, in which.

DETAILED DESCRIPTION OF THE EXAMPLE EMBODIMENTS

Figure 1:
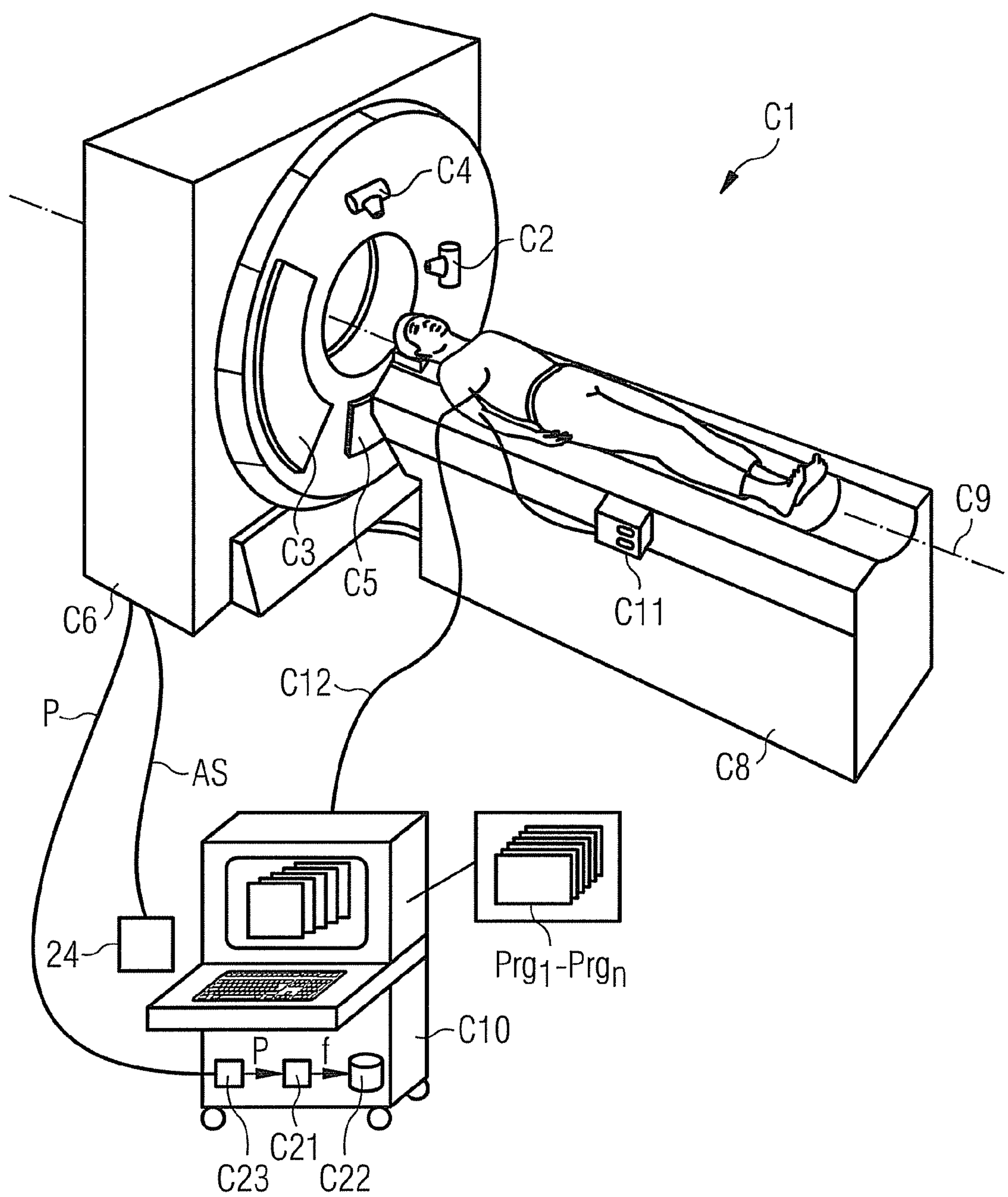
FIG. 1: shows a first schematic view of an example embodiment of a computed tomography system having an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first shows a schematic view of a first computed tomography system C1 having an image reconstruction apparatus C21. In the gantry housing C6 there is contained a closed gantry (not shown here) on which a first X-ray tube C2 is arranged with an oppositely disposed detector C3. Optionally, a second X-ray tube C4 is arranged with an oppositely disposed detector C5 in the CT system shown here, such that a higher time resolution can be achieved by way of the additionally available emitter/detector combination, or "dual energy" examinations can also be performed when different X-ray energy spectra are used in the emitter/detector systems.

The CT system C1 also has a patient table C8 on which a patient can be moved into the measuring field during the examination along a system axis C9, wherein the scanning itself can take place both as a pure circular scan without feeding movement of the patient exclusively in the examination region of interest. In the process the X-ray source C2 or C4 rotates around the patient in each case. At the same time the detector C3 or C5 co-rotates in parallel opposite the X-ray source C2 or C4 respectively in order to capture projection measured data which are then used for reconstructing slices. As an alternative to a sequential scan in which the patient is moved incrementally through the examination field between the individual scans it is of course also possible to perform a spiral scan in which the patient is moved continuously through the examination field between X-ray tube C2 or C4 and detector C3 or C5 along the system axis C9 during the rotating scanning by means of the X-ray radiation. In the case of a spiral scan, owing to the movement of the patient along the axis C9 and the simultaneous rotation of the X-ray source C2 or C4, a helical path is produced for the X-ray source C2 or C4 relative to the patient during the measurement.

The CT system C10 is controlled by way of a control and computing unit C10 having computer program code $Prg_1$ to $Prg_n$ that is resident in a memory. Acquisition control signals AS can be transmitted from the control and computing unit C10 via a control interface 24 in order to control the CT system C1 according to specific measurement protocols.

The projection measured data P acquired by the detector C3 or C5 (hereinafter also referred to as raw data) are passed to the control and computing unit C10 via a raw data interface C23. Said raw data p are then—possibly after suitable preprocessing—processed further in an image reconstruction component C21. In this exemplary embodiment the image reconstruction component C21 is implemented on a processor in the control and computing unit C10 in the form of software, e.g. in the form of one or more of the computer program codes $Prg_1$ to $Prg_n$. The image data f reconstructed by the image reconstruction component C21 are then stored in a memory C22 of the control and computing unit C10 and/or output in the usual way on the monitor screen of the control and computing unit C10. They can also be fed via an interface not shown in FIG. 1 into a network connected to the computed tomography system C1, for example into a radiological information system (RIS), and stored in a mass storage device that is accessible there or output as images.

In addition the control and computing unit C10 can also perform the function of an ECG, a cable C12 being used between patient and control and computing unit C10 to derive the ECG potentials. In addition the CT system C1 shown in FIG. 1 also has a contrast agent injector C11 via which contrast agent can additionally be injected into the patient's bloodstream so that the vessels of the patient, in particular the ventricles of the beating heart, can be visualized more clearly. Furthermore this also affords the possibility of performing perfusion measurements, to which the proposed method is likewise suited.

Figure 2:
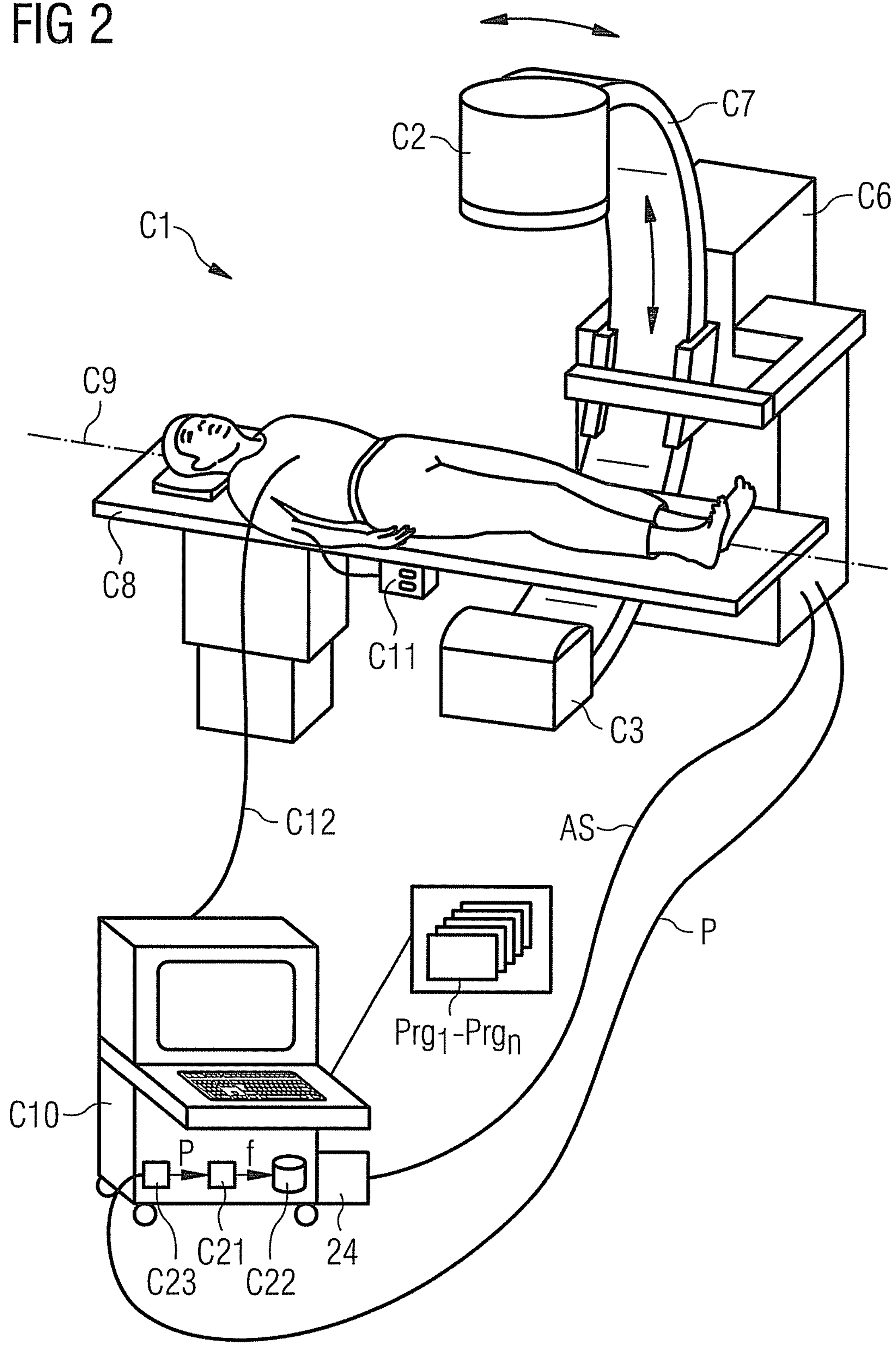
FIG. 2: shows a second schematic view of an example embodiment of a computed tomography system having an image reconstruction component.

FIG. 2 shows a C-arm system in which, in contrast to the CT system shown in FIG. 1, the housing C6 carries the C arm C7 to which the X-ray tube C2 is secured on one side and the oppositely disposed detector C3 is secured on the other side. To perform a scan the C arm C7 is likewise pivoted around a system axis C9 so that scanning can take place from a plurality of scanning angles and corresponding projection data P can be determined from a plurality of projection angles. The C-arm system C1 of FIG. 2, like the CT system from FIG. 1, has a control and computing unit C10.

Since in principle the same reconstruction methods for generating slices can be applied in the two tomographic X-ray systems shown, the method according to an embodiment of the invention can also be used for both systems. Furthermore the method according to an embodiment of the invention can also be used in principle for other CT systems, e.g. for CT systems having a detector forming a complete ring.

Figure 3:
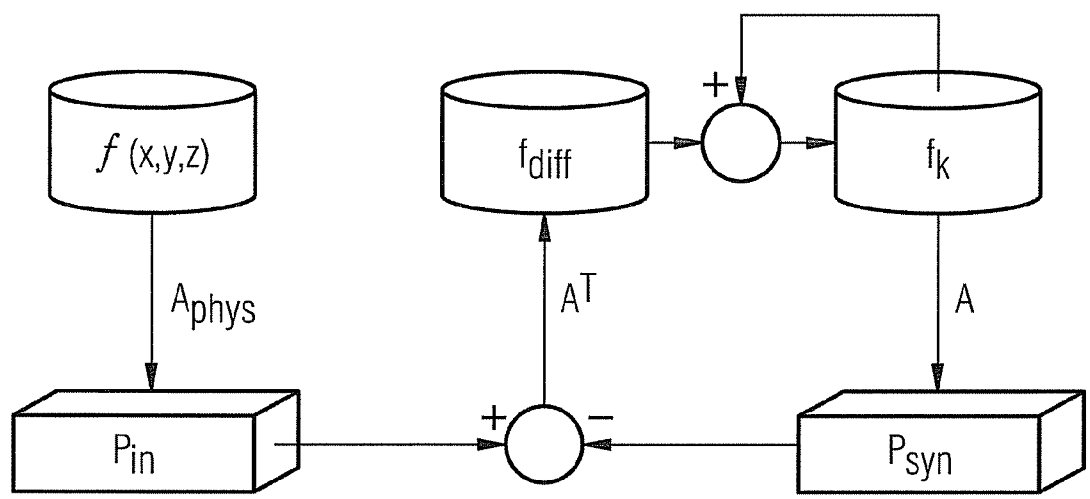
FIG. 3: shows a schematic of an iterative algorithm.

An iterative method whose basic principle is illustrated in FIG. 3 is used for reconstructing the slices from the recorded projections. The input data $p_{in}$ are the recorded projections. These are obtained—considered mathematically—by applying the actual, i.e. present in reality, projector $A_{phys}$ to the actual attenuation distribution f(x,y,z) of the examination object: $p_{in}=A_{phys}$ f(x,y,z). The aim of the iterative algorithm is to determine from the input data $p_{in}$ an attenuation distribution f, i.e. a two-dimensional slice or a three-dimensional volume distribution of the attenuation, which corresponds as closely as possible to the actual attenuation distribution f(x,y,z) of the examination object.

For that purpose the operator A, a constructed projector, is intended to simulate the measuring process as precisely as possible. The projector A is a model of the projector $A_{phys}$ present in reality, i.e. of the measuring process. Variables incorporated into the operator A are for example a model of the tube focus, the detector aperture, detector crosstalk, etc.

An example of a suitable projector A is the so-called Josephson projector. In this case line integrals are modeled by means of pencil beams, i.e. beams with the extension zero. Each vertex, i.e. each volume element, of the image volume is linked with a basic function, e.g. trilinearly, such that the contribution of the vertex to the line integral can be interpolated accordingly. The respective integral is then entered as a projection value into the respective detector bin. Operators of this type are known per se and described e.g. in P. M. Joseph, "An improved algorithm for reprojection rays through pixel images", IEEE Trans. Med. Imag. 1:193-196, 1982, the entire contents of which are hereby incorporated herein by reference.

Further projectors are described e.g. in K. Mueller, R. Yagel, J. J. Wheller: "Fast implementations of algebraic methods for three-dimensional reconstruction of cone-beam data", IEEE Trans. Med. Imag. 18 (6): 538-548, 1999, the entire contents of which are hereby incorporated herein by reference.

The slice, i.e. the calculated attenuation distribution, is obtained from the projections by means of the operator $A^T$ adjoint to A: $f=A^T$ p. The back-projector $A^T$ represents a non-exact reconstruction method. The 3-dimensional radon transform necessary for an exact solution is therefore not performed completely. Accordingly the actual attenuation distribution f(x,y,z) is determined only approximately by applying the back-projector $A^T$ to the input data $p_{in}$. For this reason an iterative approach is applied in order to approximate as closely as possible to the actual attenuation distribution f(x,y,z) within a plurality of iteration cycles.

A first attenuation distribution $f_0$ is calculated by way of an initial reconstruction, i.e. by way of a first application of the back-projector $A^T$ to the input data $p_{in}$; the operation in this case concerns the first estimated image. This is not shown in FIG. 3. The variable $f_0$ corresponds to the variable $f_k$ of FIG. 3 in the zeroth iteration cycle. Following on from this, synthetic projections are calculated using the projector A: $P_{syn}=A\ f_0$. Synthetic, in this context, means that a calculated variable is involved, not measured data.

Following this, the difference between the input data $p_{in}$ and the synthetic projections $P_{syn}$ is determined. This residuum $p_{in}-P_{syn}$ is used in turn in order to calculate a new attenuation distribution using the back-projector $A^T$, namely the differential attenuation distribution $f_{diff}$: $f_{diff}=A^T(p_{in}-P_{syn})$. The difference $p_{in}-P_{syn}$ is therefore back-projected using the operator $A^T$ in order to calculate the residue image $f_{diff}$.

The addition of the differential attenuation distribution $f_{diff}$ and the attenuation distribution $f_0$ in the zeroth iteration cycle results in an improved attenuation distribution $f_1$. This corresponds in FIG. 3 to the variable $f_k$ of the first iteration cycle. From now on the described approach is iterated. In each iteration cycle the newly calculated data $P_{syn}$ are therefore compared with the measured data $p_{in}$. By this, the iteration image $f_k$ is more closely aligned with the measured data in each iteration cycle.

In order to express the described iterative approach mathematically, the iteration equation is implemented with the aid of the steepest descent method. To that end z(f) is defined as the cost function of the attenuation distribution that is to be minimized:

$$z(f) = \|Af - p_{in}\|_K^2 + \beta \cdot \sum_{i,j}^{N} d_{i,j} \cdot V(f_i - f_j) \qquad \text{Formula (1)}$$

In this case the scalar product is defined as follows:

$$\|Af-p_{in}\|_K^2=(Af-p_{in})^T \cdot K \cdot (Af-p_{in})$$

where K is a matrix operation, namely a convolution operation using a conventional CT reconstruction kernel or reconstruction filter.

With the aid of the potential function V, the regularization term $$R(f) = \beta \cdot \sum_{i,j}^{N} d_{i,j} \cdot V(f_i - f_j)$$

links the grayscale values $f_i$ and $f_j$ of adjacent image voxels with index i and j and with inverse distance $1/d_{i,j}$. By way of this regularization term certain conditions can be enforced between the values of adjacent pixels.

The gradient $$\frac{dz(f)}{df}$$

results in:

$$\frac{dz(f)}{df} = 2 \cdot A^T K(Af - p_{in}) + \beta \cdot \sum_{i=1}^{N} e_i \sum_{j=1}^{N} d_{i,j} \cdot \frac{dV(f_i - f_j)}{df} \qquad \text{Formula (2)}$$

where $e_i=(0, \ldots, 0, 1, 0, \ldots 0)$ forms a unit vector with a 1 at the i-th position.

In the case of a quadratic potential function V, the regularization term can be linearized: R(f)=R·f, as is shown in J. Sunnegardh: "Combining Analytical and Iterative Reconstruction in Helical Cone-Beam CT", Thesis No. 1301, Linkoping Studies in Science and Technology, 2007, the entire contents of which are hereby incorporated herein by reference.

In this case the iterated attenuation distribution $(f)_k$ could be calculated in the k-th iteration step as follows, where the attenuation distribution of the k-th iteration step $(f)_k$ is incorporated linearly into the update equation (3):

$$(f)_{k+1}=(f)_k+\alpha\cdot\mathrm{grad}_f(z) \quad \text{Formula (3)}$$

It can be shown (see the above-cited work by J. Sunnegardh) that the iteration formulated in formula (3) for $k\to\infty$ converges toward the grayscale value distribution $$(f)_\infty=(A^TKA+\beta\cdot R)^{-1}A^TKp_{in} \quad \text{Formula (4)}$$

Equation (4) applies only if the potential function V is quadratic, and hence the so-called influence function dV/df is linear. Only then is the update equation (3) a linear transformation of f. (Convergence is present if the eigenvalues of the operator $T=(A^TKA+\beta R)^{-1}$ all lie inside the unit circle.)

In traditional convolution back-projection the image characteristics, i.e. the image sharpness and the image noise, are set by means of the selectable convolution kernel. For example, a very sharp kernel can be used which leads to sharp edges and a strong noise in the images, or, for example, a soft kernel can be used which establishes a correlation between adjacent pixels and consequently has a noise-reducing effect and blurs edges.

In the iterative reconstruction, in contrast, the regularization term R determines—in addition to the projector/back-projector pair—the image characteristics. A suitable regularization term R can be determined from formula (4). To that end a specific characteristic is specified for the definitive convergence image $(f_\infty)$ and an R determined which leads to a convergence image $(f_\infty)$ having such a characteristic.

A regularization term R determined in this way corresponds to a high-pass filter. If this is applied within the iterative method, the update image is high-pass-filtered in each iteration cycle, such that an image having the desired characteristics is obtained following completion of the iteration.

A further aim is now not only to obtain the desired image characteristics, but also to set a desired contrast/noise ratio. In this case the contrasts within an image are produced as grayscale value differences between neighboring pixels. High contrast values are important for CT images because by this means it is easier to identify structures, e.g. the presence of a tumor in a tissue.

In the case of a nonlinear influence function dV/df, the update formula cannot be set up according to formula (3). Rather, the following update equation is used:

$$(f)_{k+1}=(f)_k-\alpha_k\cdot[(2\cdot A^TK(A\cdot(f)_k-p_{in})+\beta_k(df)\cdot R\cdot(f)_k)] \quad \text{Formula (5)}$$

The parameter $\alpha_k$ controls the convergence speed of the iteration. The variable $\beta_k=\beta_k(\mathrm{df})$ controls the strength of the admixture of the high-pass-filtered regularization image $R\cdot(f)_k$.

In order to obtain a high-contrast image as explained above, $\beta_k$ is chosen as a function of the image contrast df. $\beta_k$ is a three-dimensional matrix, wherein each matrix entry is assigned to a pixel of the image volume. The entries of the matrix $\beta_k$ therefore specify a weighting of the image contrast value for each pixel. The index k indicates that $\beta_k$ accordingly changes from iteration to iteration, since the contrast values corresponding to the current iteration image $(f)_k$ at any one time are expressed by $\beta_k$. The contrast values of the image volume df that are required for determining $\beta_k$ can be acquired by applying an edge detector, e.g. a Laplace operator, to the image data $(f)_k$. For that purpose the image volume $(f)_k$ is filtered by means of an edge detector.

The effect of using $\beta_k$ in formula (5) is that smoothing is performed for homogeneous surfaces and hence the noise is reduced, whereas no smoothing takes place beyond edges, thus ensuring a high contrast is preserved.

An example possibility of formulating the contrast dependence of $\beta_k$ is the following:

$$\beta_k(df)=\beta_k^0 e^{-\left(\frac{df}{\sigma}\right)^2} \quad \text{Formula (6)}$$

The parameter $\sigma$ corresponds to the image noise, which can be determined for example as a global noise mean value in the update image $(f)_k$. The selectable parameter $\beta_k^0$ denotes the scalar regularization strength effective in the k-th iteration. This value can be chosen to be equal or different for each iteration loop.

For large contrast values df, the variable $\beta_k(\mathrm{df})$ is almost zero, with the result that the regularization image $R\cdot(f)_k$ is virtually suppressed in the update equation (5). This means that in the calculation of the update image no smoothing takes place at positions of an image where edges are present. For small values df, $\beta_k(\mathrm{df})$ becomes large, with the result that according to formula (5) the regularization image $R\cdot(f)_k$ is subtracted from $f_k$. Since R is a high pass and correspondingly $(1-R)$ is a low pass, small contrast values df cause a low-pass filtering of the image. This is equivalent to a noise-reducing smoothing of the image. Thus, the effect of $\beta_k(\mathrm{df})$ is that high-contrast edges are preserved, whereas conversely smoothing takes place in the homogeneous image area—i.e. in low-contrast regions of the image.

The described approach can be applied for each two-dimensional slice. In this case the regularization according to formula (5) is performed layer by layer on the axial update images. The regularization filter R is two-dimensional in this instance. It is also possible to extend the two-dimensional regularization filter R into the third dimension. By this, the quantum statistics and hence the signal-to-noise ratio (SNR) can continue to be improved. To that end the image vector is arranged in layers. Let $(f^c)_k$ designate the image layer c currently to be filtered in the k-th iteration, $(f^{c+1})_k$ the upper and $(f^{c-1})_k$ the lower neighbor layer.

A z-filter, i.e. the filter in the axial direction, is applied pixel by pixel: in the pixel $\vec{r}=(x_0,y_0)$ the filtered central image $(f^c)_k$ results in $$(\tilde{f}^c)_k(\vec{r})=(f^c)_k(\vec{r})-\vec{e}_2\cdot\begin{pmatrix}(f^{c-1})_k(\vec{r})-(R\cdot(f^{c-1})_k(\vec{r}))\\(f^c)_k(\vec{r})-(R\cdot(f^c)_k(\vec{r}))\\(f^{c+1})_k(\vec{r})-(R\cdot(f^{c+1})_k(\vec{r}))\end{pmatrix}*\vec{l} \quad \text{Formula (7)}$$

where $\vec{l}$ represents a filter kernel of length 3 with low-pass effect, e.g.

$$\vec{l}=\begin{pmatrix}1/4\\1/2\\1/4\end{pmatrix}.$$

The method can also be adapted to filter kernels $\vec{l}$ having a greater range. The operator * denotes the convolution operation, and $\vec{e}_2=(0,1,0)$.

The overall result yielded is a high-pass-filtered regularization image $(\tilde{f}^c)_k(\vec{r})$. Formula (5) thus becomes $$(f^c)_{k+1}=(f^c)_k-\alpha_k\cdot\lfloor 2\cdot A^T K(A(f^c)_k-p_{in})+\beta_k(df)\cdot(\tilde{f}^c)_k\rfloor \qquad \text{Formula (8)}$$

The variable $\beta_k$ is determined in principle as explained hereintofore in the case of formula (6), where the contrast df of a pixel now indicates not only the differences from the neighboring pixels in the same slice, but also the differences between the pixel and the adjacent pixels of the neighboring layers.

In the general case the regularization filter R can also be dependent on k, i.e. the regularization kernel can be changed during the iteration.

The invention has been described hereintofore with reference to an exemplary embodiment. It is to be understood that numerous variations and modifications are possible without leaving the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing an image of an examination object from measured data, the measured data being captured during a rotating movement of a radiation source of a computed tomography system around the examination object, the method comprising:

determining, by a control and computing unit, different iteration images of the examination object, successively, from the measured data by use of an iterative algorithm, during each iteration of the iterative algorithm, high-pass-filtering, by the control and computing unit, a current one of the iteration images, determining a variable based on a contrast to noise ratio of the current one of the iteration images, the variable providing location dependent contrast information of the current one of the iteration images, and weighting, by the control and computing unit, the high-pass-filtered current one of the iteration images as a function of contrast among pixels of the current one of the iteration images using the variable; and determining a next one of the iteration images based on the current one of the iteration images and the weighted current one of the iteration images, wherein an amount of reduction in noise associated with the current one of the iteration images depends on the location dependent contrast information, and a level of admixture of the current one of the iteration images and the weighted current one of the iteration images for determining the next one of the iteration images is determined using the variable.

2. The method as claimed in claim 1, wherein the variable contains contrast information for each pixel of the current iteration image at a given time.

3. The method as claimed in claim 1, wherein the variable is written as $$\beta = \beta^0 e^{-\left(\frac{df}{\sigma}\right)^2},$$

where $\beta^0$ is a parameter denoting a scalar regularization strength effective in the current iteration, df is a contrast value and $\sigma$ is a noise value of the current one of the iteration images.

4. The method as claimed in claim 1, wherein the determining determines the next one of the current iteration images by applying the weighted current one of the iteration images to the current one of the iteration images.

5. A Computer Tomography (CT) system for reconstructing an image of an examination object from measured data, the measured data being captured during a rotating movement of a radiation source of the CT system around the examination object, the CT system comprising:

a control and computing unit configured to, determine different iteration images of the examination object, successively, from the measured data by use of an iterative algorithm, during each iteration of the iterative algorithm, the control and computing is configured to, high-pass-filter a current one of the iteration images, determine a variable based on a contrast to noise ratio of the current one of the iteration images, the variable providing location dependent contrast information of the current one of the iteration images, and weight the high-pass-filtered current one of the iteration images as a function of contrast among pixels of the current one of the iteration images using the variable; and determine a next one of the iteration images based on the current one of the iteration images and the weighted current one of the iteration images, wherein an amount of reduction in noise associated with the current one of the iteration images depends on the location dependent contrast information, and a level of admixture of the current one of the iteration images and the weighted current one of the iteration images for determining the next one of the iteration images is determined using the variable.

6. A non-transitory computer readable medium including a computer program product, the computer program product comprising instructions, which when executed on a computer, causes the computer to perform functions for reconstructing an image of an examination object from measured data, the measured data being captured during a rotating movement of a radiation source of a computed tomography (CT) system around the examination object including:

determining different iteration images of the examination object, successively, from the measured data by use of an iterative algorithm, during each iteration of the iterative algorithm, high-pass-filtering a current one of the iteration images, determining a variable based on a contrast to noise ratio of the current one of the iteration images, the variable providing location dependent contrast information of the current one of the iteration images, and weighting the high-pass-filtered current one of the iteration images as a function of contrast among pixels of the current one of the iteration images using the variable; and determining a next one of the iteration images based on the current one of the iteration images and the weighted current one of the iteration images, wherein an amount of reduction in noise associated with the current one of the iteration images depends on the location dependent contrast information, and a level of admixture of the current one of the iteration images and the weighted current one of the iteration images for determining the next one of the iteration images is determined using the variable.

7. The method as claimed in claim 1, wherein the iterative algorithm enables a noise reduction based on the variable at low-contrast locations of each of the iteration images.

8. The CT system as claimed in claim 5, wherein the iterative algorithm enables a noise reduction based on the variable at low-contrast locations of each of the iteration images.

9. The non-transitory computer readable medium as claimed in claim 6, wherein the iterative algorithm enables a noise reduction based on the variable at low-contrast locations of each of the iteration images.

10. The method as claimed in claim 1, wherein high-pass filtering includes applying a regularization term to the current one of the iteration images, the regularization term indicating a desired image characteristic of the reconstructed image.

11. The method as claimed in claim 1, wherein the determining a next one of the iteration images determines the next one of the iteration images by subtracting the weighted current one of the iteration images from the current one of the iteration images.

12. The method as claimed in claim 11, wherein the determining a next one of the iteration images multiplies the weighted current one of the iteration images by a convergence factor prior to subtracting the weighted current one of the iteration images from the current one of the iteration images.

13. The CT system as claimed in claim 5, wherein the control and computing unit is configured to high-pass filter the current one of the iteration images by applying a regularization term to the current one of the iteration images, the regularization term indicating a desired image characteristic of the reconstructed image.

14. The CT system as claimed in claim 5, wherein the control and computing unit is configured to determine the next one of the iteration images by subtracting the weighted current one of the iteration images from the current one of the iteration images.

15. The CT system as claimed in claim 14, wherein the control and computing unit is configured to multiply the weighted current one of the iteration images by a convergence factor prior to subtracting the weighted current one of the iteration images from the current one of the iteration images.

16. The non-transitory computer readable medium as claimed in claim 6, wherein the high-pass filtering includes applying a regularization term to the current one of the iteration images, the regularization term indicating a desired image characteristic of the reconstructed image.

17. The non-transitory computer readable medium as claimed in claim 6, wherein the determining a next one of the iteration images determines the next one of the iteration images by subtracting the weighted current one of the iteration images from the current one of the iteration images.

18. The non-transitory computer readable medium as claimed in claim 17, wherein the determining a next one of the iteration images multiplies the weighted current one of the iteration images by a convergence factor prior to subtracting the weighted current one of the iteration images from the current one of the iteration images.

* * * * *